United States Patent
Duysens et al.

[11] Patent Number: 6,104,960
[45] Date of Patent: Aug. 15, 2000

[54] SYSTEM AND METHOD FOR PROVIDING MEDICAL ELECTRICAL STIMULATION TO A PORTION OF THE NERVOUS SYSTEM

[75] Inventors: Victor P. J. Duysens, Grevenbicht, Netherlands; Robert M. Pearson, Woodbury; Eric H. Bonde, Victoria, both of Minn.

[73] Assignee: Medtronic, Inc., Minneapolis, Minn.

[21] Appl. No.: 09/114,493

[22] Filed: Jul. 13, 1998

[51] Int. Cl.[7] ........................................... A61N 1/05
[52] U.S. Cl. ............................................... 607/117
[58] Field of Search ................................ 607/116, 117

[56] References Cited

U.S. PATENT DOCUMENTS

| | | |
|---|---|---|
| 3,416,534 | 12/1968 | Quinn . |
| 3,472,234 | 10/1969 | Tachick . |
| 4,000,745 | 1/1977 | Goldberg . |
| 4,027,677 | 6/1977 | Schulman et al. . |
| 4,044,774 | 8/1977 | Corbin et al. . |
| 4,156,429 | 5/1979 | Amundson . |
| 4,273,137 | 6/1981 | Pravoverov et al. . |
| 4,328,812 | 5/1982 | Ufford et al. . |
| 4,633,889 | 1/1987 | Talalla et al. . |
| 5,524,619 | 6/1996 | Ouchi et al. . |

*Primary Examiner*—Scott M. Getzow
*Attorney, Agent, or Firm*—Thomas F. Woods; Michael J. Jaro; Harold Patton

[57] ABSTRACT

A system and method for providing medical electrical stimulation to a portion of the nervous system. The system includes a rigid hollow needle having a lumen, a flexible lead body disposed within the lumen of the needle, the lead body having a insulated coiled proximal section and an electrode section, the proximal section comprising a conductor which is coiled and insulated, the electrode section comprises a portion of the coiled conductor which is not insulated. In an alternative embodiment the electrode section features a crimp core around which a distal end of the coiled conductor which is not insulated is crimped, the rigid hollow needle is metal but which is partially covered along its outer surface with an insulation. In still further embodiments the flexible lead body has a stylet lumen therein and the lead body also has a connector pin for electrically connecting the electrical conductor to a pulse generator. Preferably this connector pin located on a proximal end of the lead body and having a diameter no greater than the inner diameter of the needle. A method of providing temporary electrical stimulation to the sacral nerve is also disclosed.

22 Claims, 7 Drawing Sheets

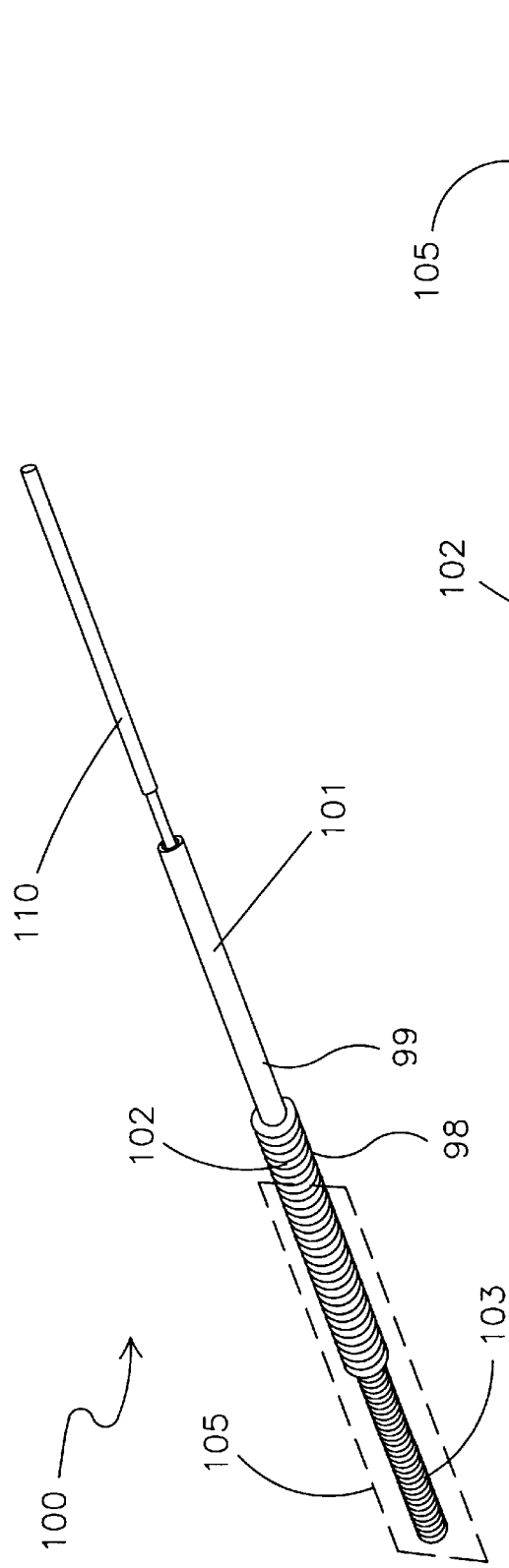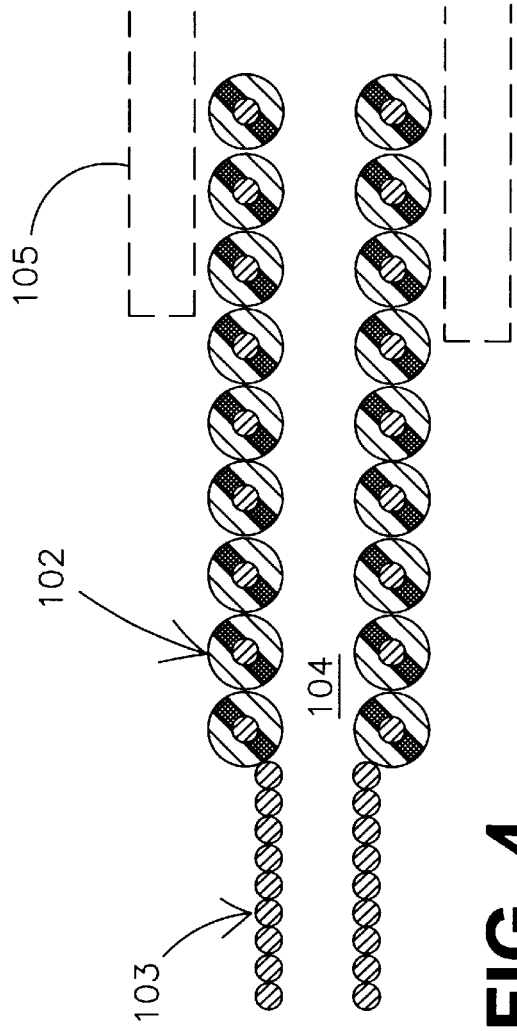

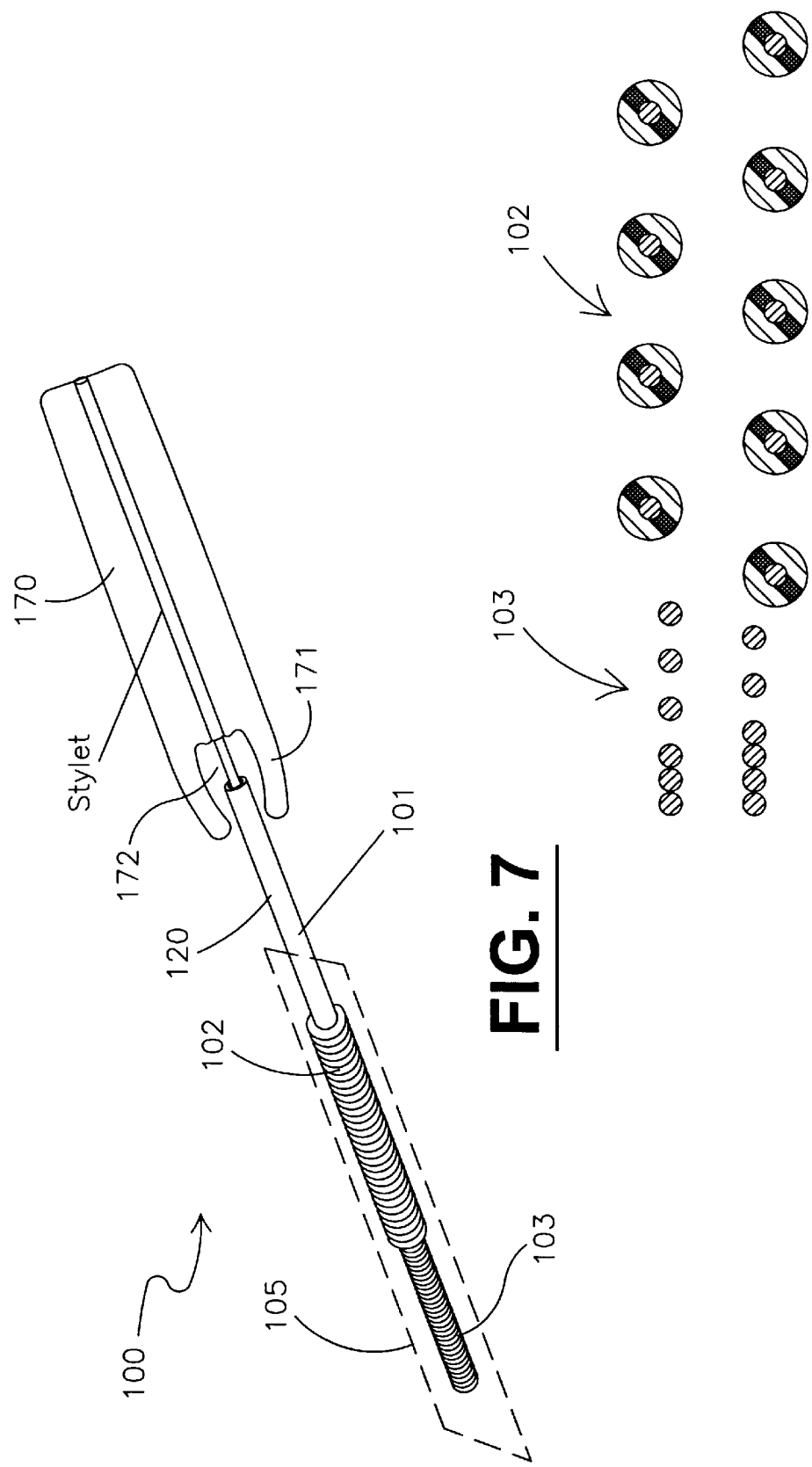

SYSTEM AND METHOD FOR PROVIDING MEDICAL ELECTRICAL STIMULATION TO A PORTION OF THE NERVOUS SYSTEM

FIELD OF THE INVENTION

This invention relates to system and method for providing medical electrical stimulation to a portion of the nervous system and specifically to a sacral medical electrical lead which may be implanted and reliably fixed for a temporary period of time within the sacrum in a minimally invasive manner.

BACKGROUND OF THE INVENTION

The present invention relates to the art of selective nerve stimulation. The invention finds particular application in conjunction with urination control and will be described with particular reference thereto. The invention is also applicable to control other aspects of the nervous system, such as for fecal incontinence, penile erection, and others.

The organs involved in bladder, bowel, and sexual function receive much of their control via the second, third, and fourth sacral nerves, commonly referred to as S2, S3 and S4 respectively. Electrical stimulation of these various nerves has been found to offer some control over these functions. Several techniques of electrical stimulation may be used, including stimulation of nerve bundles within the sacrum.

The sacrum, generally speaking, is a large, triangular bone situated at the lower part of the vertebral column, and at the upper and back part of the pelvic cavity. The spinal canal runs throughout the greater part of this bone. It lodges the sacral nerves, and is perforated by the anterior and posterior sacral foramina through which these pass out.

Several systems of stimulating sacral nerves exist. For example, U.S. Pat. No. 4,607,639 to Tanagho et al. entitled "Method and System for Controlling Bladder Evacuation", incorporated herein by reference, and the related U.S. Pat. No. 4,739,764 to Lue et al. entitled "Method for Stimulating Pelvic Floor Muscles for Regulating Pelvic Viscera", also incorporated herein by reference, disclose implanting an electrode on at least one nerve controlling the bladder. In one embodiment the electrode is percutaneously implanted through the dorsum and the sacral foramen of the sacral segment S3 for purposes of selectively stimulating the S3 sacral nerve. The electrode is positioned using a hollow spinal needle through a foramen (a singular foramina) in the sacrum. The electrode is secured by suturing the lead body in place. U.S. Pat. No. 4,569,351 to Tang entitled "Apparatus and Method for Stimulating Micturition and Certain Muscles in Paraplegic Mammals", incorporated herein by reference, discloses use of electrodes positioned within the sacrum to control bladder function.

Typically electrical stimulation of the nerves within the sacrum is accomplished by positioning a lead having at least one electrode at its distal end through a foramen of the sacrum and proximate the nerve. Not all patients, however, are suitable for such stimulation. In fact, at present there is not a reliable screening tool to identify patients who would or would not benefit from sacral nerve stimulation other than to actually stimulate such nerves.

Placing a lead into the sacrum in order to assess the efficacy of sacral nerve stimulation may be performed percutaneously, that is, simply using a needle. Leads implanted in such a manner, however, have to date been difficult to reliably anchor so that the electrode remains in the correct position. Techniques such as taping the exterior lead body to the patient are not wholly satisfactory in terms of both the electrode placement as well as patient comfort. Other techniques which are effective to anchor a sacral lead, such as screwing the lead to the sacral bone, are much too invasive for an initial screening procedure. An additional method of anchoring such a lead may be seen in the pending U.S. patent application Ser. No. 08/811,054 of Moumane et al., "Sacral Medical Electrical Lead" filed Mar. 3, 1997 assigned to the assignee of the present invention and incorporated herein by reference. That application generally concerned a sacral lead which had a notched section in which the insulation of the lead body presents a macroscopically roughened surface to engage into tissue without causing damage to the tissue. One drawback to this design, however, is that any pulling or tugging on the proximal end of the lead body outside the body could be directly communicated to the electrode section, thus creating a higher likelihood of electrode dislodgment and poor stimulation.

Thus there exits a need for a medical electrical lead which may be safely and effectively implanted into the sacrum and anchored within in a minimally invasive manner, but which further prevents any pulling or tugging on the proximal end of the lead body outside the body to be directly communicated to the electrode.

SUMMARY OF THE INVENTION

A system and method for providing medical electrical stimulation to a portion of the nervous system. The system includes a rigid hollow needle having a lumen, a flexible body disposed within the lumen of the needle, the lead body having a insulated coiled proximal section and an electrode section, the proximal section comprising a conductor which is coiled and insulated, the electrode section comprises a portion of the coiled conductor which is not insulated. In an alternative embodiment the electrode section features a crimp core around which a distal end of the coiled conductor which is not insulated is crimped, the rigid hollow needle is metal but which is partially covered along its outer surface with an insulation. In still further embodiments the flexible lead body has a stylet lumen therein and the lead body also has a connector pin for electrically connecting the electrical conductor to a pulse generator. Preferably this connector pin located on a proximal end of the lead body and having a diameter no greater than the inner diameter of the needle. A method of providing temporary electrical stimulation to the sacral nerve is also disclosed.

BRIEF DESCRIPTION OF THE DRAWINGS

FIG. 3 is a perspective view of a medical electrical lead disposed through a needle according to the present invention.

FIG. 4 is a sectional view of the distal end of the lead of FIG. 3.

FIG. 7 is a perspective view of an additional embodiment of a medical electrical lead disposed through a needle according to the present invention.

FIG. 8 is a sectional view of the distal end of an additional embodiment of a medical electrical lead according to the present invention.

The FIGS. are not necessarily to scale.

DETAILED DESCRIPTION OF THE PREFERRED EMBODIMENTS

As discussed above, the present invention provides a system and method for providing medical electrical stimulation to a portion of the nervous system. In particular the present invention features a lead which permits temporary electrical stimulation of one or more sacral nerves. This temporary stimulation is necessary in order to identify those patients who will be best treated through sacral nerve stimulation as well as those who will not. As discussed above leads used for such temporary stimulation must meet several requirement. First any such lead used must be able to be removed in a smooth manner. Also, any lead must minimize migration or movement of the lead and particularly of the electrode while it is implanted. The lead should also be able to be easily introduced, such as through a simple needle while also permitting an easy connection to an external device. Finally, it is also extremely important that any such lead be able to provide longitudinal strain relief such that any pulling or tugging on the outside end of the lead will not be automatically translated to the electrode.

The system of the present invention meets these criteria. The system includes a rigid hollow needle having a lumen, a flexible lead body disposed within the lumen of the needle, the lead body having a insulated coiled proximal section and an electrode section, the proximal section comprising a conductor which is coiled and insulated, the electrode section comprises a portion of the coiled conductor which is not insulated. In an alternative embodiment the electrode section features a crimp core around which a distal end of the coiled conductor which is not insulated is crimped, the rigid hollow needle is metal but which is partially covered along its outer surface with an insulation. In still further embodiments the flexible lead body has a stylet lumen therein and the lead body also has a connector pin for electrically connecting the electrical conductor to a pulse generator. Preferably this connector pin located on a proximal end of the lead body and having a diameter no greater than the inner diameter of the needle.

Figure 1:
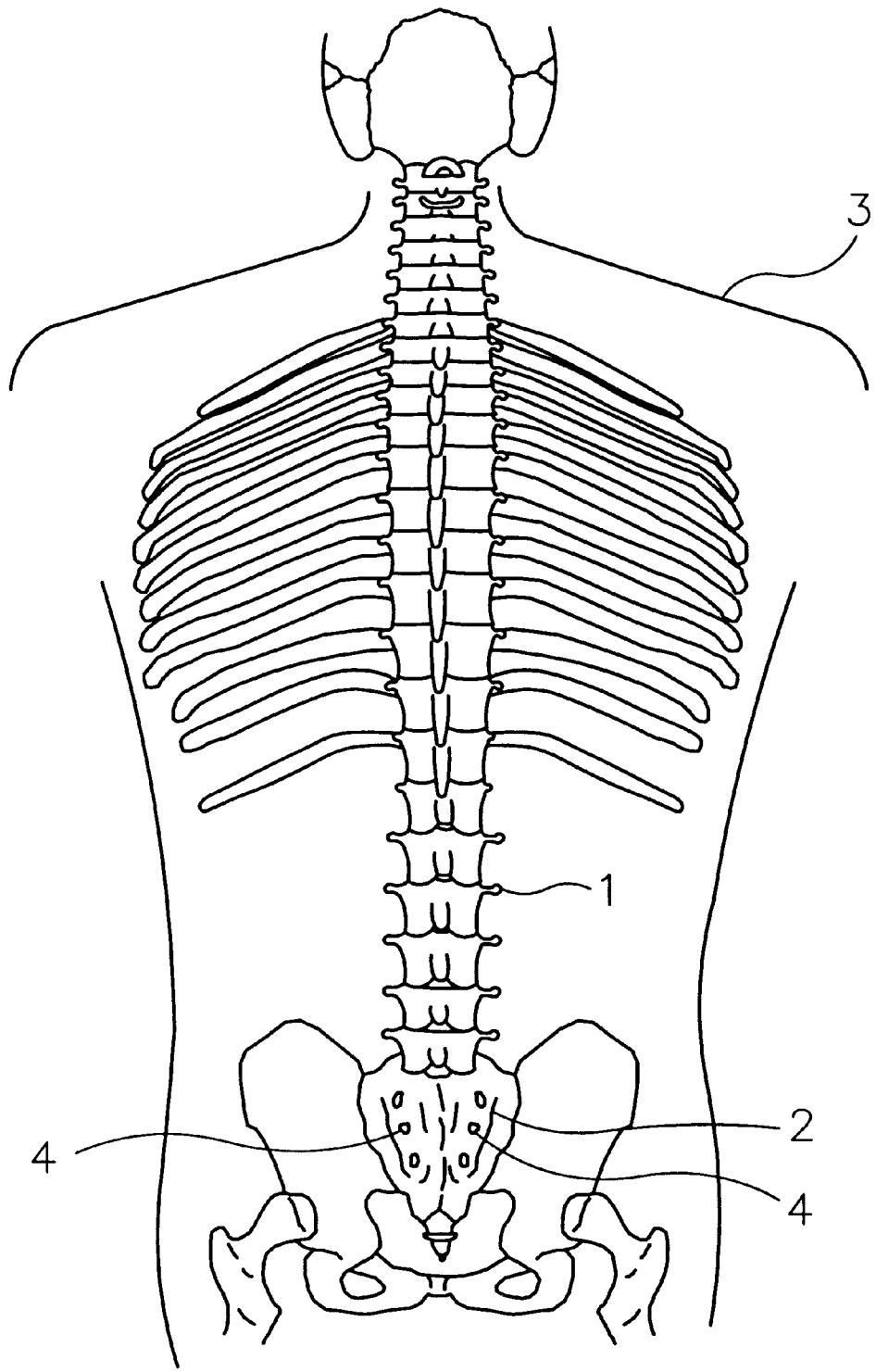
FIG. 1 is a posterior view of the spinal column showing the location of the sacrum relative to an outline of a body.

FIG. 1 is a posterior view of the spinal column 1 showing the location of the sacrum 2 relative to an outline of a body 3. As seen, the sacrum 2 has a series of holes, known as foramina 4, therethrough. Each foramen 4 (as they are referred to in the singular) provides access to the sacral ventral nerves (not shown). As discussed above electrical stimulation of these nerves is useful to effect control of an organ, such as a bladder (not shown).

Figure 2A:
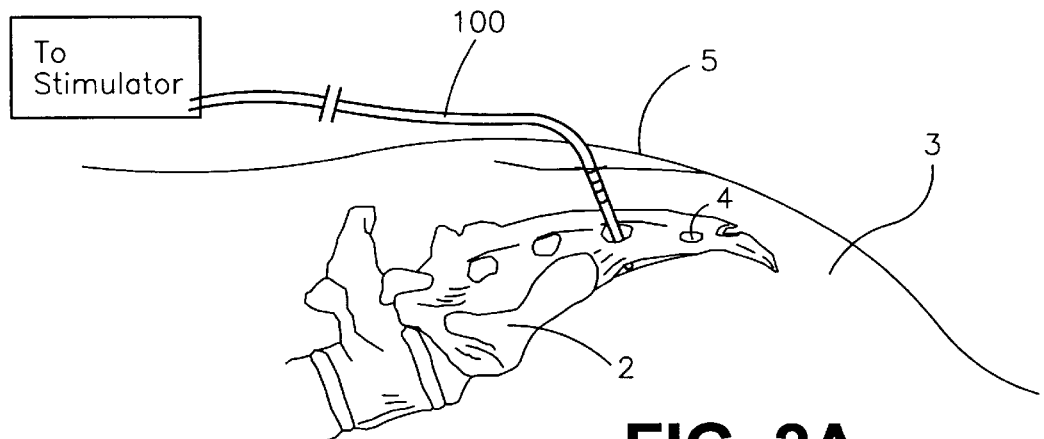
FIG. 2A is a side view of the sacrum having a lead implanted.

FIG. 2A is a side view of the sacrum having a lead implanted. As seen, the sacrum 2 has a series of foramina 4 located near the dorsal surface 5 and a patient 3. Lead 100 may be inserted using a percutaneous procedure into the foramina so that the electrode at the distal end is positioned near the sacral nerve. Once inserted lead is coupled to a stimulator, as shown. In the preferred embodiment stimulator is the Medtronic Model 3625 Test Stimulator which may further be coupled using a Medtronic Model 041827 Screener Cable Kit.

Figure 2B:
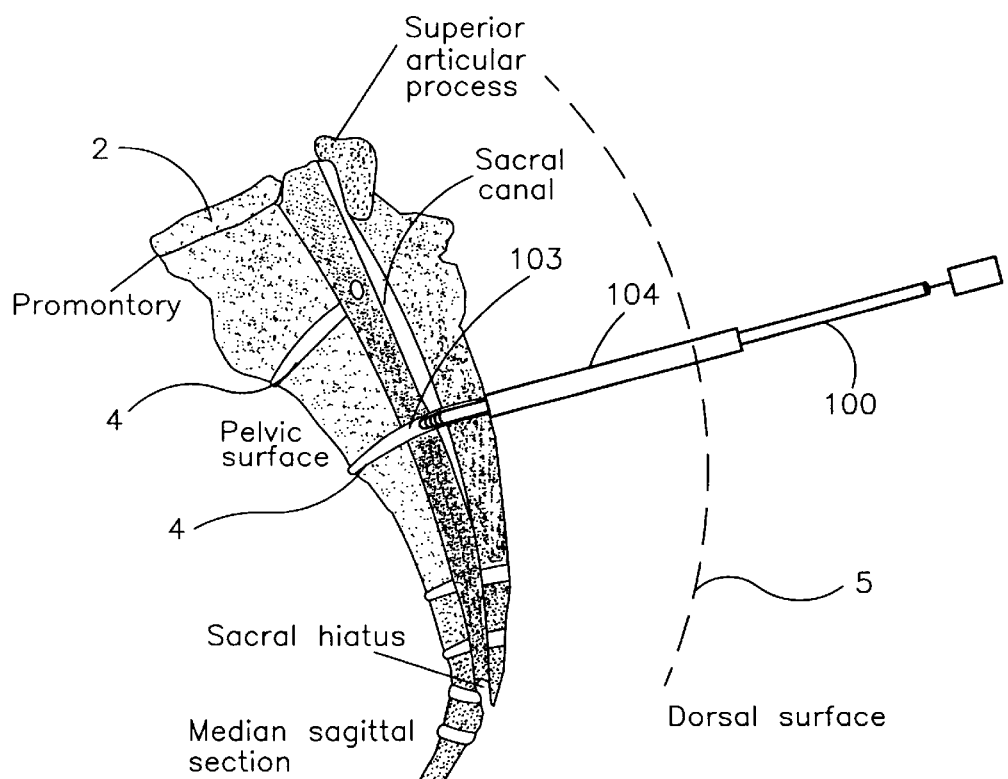
FIG. 2B is a sectional view of the sacrum showing a stimulation system which features a medical electrical lead of the preset invention placed within the sacrum.

FIG. 2B is the side sectional view of a lead 100 implanted into the sacrum using needle 104. As seen, the lead has an electrode 103 at its distal end. In typical use lead 100 having a distal electrode could be percutaneously placed on the S3 sacral nerve with the external extremity of the wire attached to the electrode then being taped to the skin, along with a stimulator coupled thereto. The patient could then resume his day-to-day lifestyle and be allowed to stimulate the nerve or nerves artificially via the stimulator (not shown in this FIG.). If the response is positive and an acceptable amount of relief is achieved, then a permanent system can be implanted. Should little or no improvement result, the same procedure could be tried again at a different location to ascertain if another nerve or nerves require stimulation. Thus, this invention contemplates not only the implantation of one or more electrodes in the sacral nervous system for controlling evacuation of a visceral organ or the like, but also contemplates use of such electrodes and procedures to rehabilitate muscle dysfunction by neuromodulation of muscular behavior.

FIG. 3 is a side view of an medical electrical lead of the present invention. As seen lead 100 has essentially three sections, connector pin 101, lead body 102, and electrode 103. Connector pin is preferably a stainless steel platinum. Likewise, electrode is preferably a stainless steel. Lead body is preferably constructed from SST 316L stainless steel multi filament wire covered by an insulation of PTFE. Of course other materials may also be selected for either the conductor or insulation. In the preferred embodiment lead body and electrode consists of a closely wound coil. This permits both the lead body to engage in a non destructive manner with the tissue so as to permit the electrode to be reliably anchored within the sacrum near a nerve while also isolating any strain from outside the body to the electrode. In the preferred embodiment lead has a total length 419+/−6 mm Electrode is preferably 10 mm in length and has a surface area of 11 sq. mm. Electrode preferably has an outer diameter of 0.6 mm as compared to the lead body which preferably has an outer diameter of 0.7 mm. This ultimately means the lead may be introduced using a 20 gauge needle. As seen, however, each section of lead body has the same internal diameter. Lead body also preferably features a series of markings, depicted here as 98, 99. Markings are preferably set at distance of 3.5 inches and 5.0 inches from the distal end of the lead and thus permit the approx. distance the lead is implanted into the patient to be estimated. Positioned within lead is stylet 110 to assist with lead handling. In an alternative embodiment the needle may be made splittable to assist in removing the lead from around the lead once the lead is implanted.

FIG. 4 is a sectional view of the distal end of the lead of FIG. 3. As seen, lead body 102 is composed of a closely wound insulated wire and electrode section 103 is comprised of the same wire which is also closely wound but which has had its outer insulation removed prior to the winding. As further seen, lead body and electrode have a center lumen 104 defined therein which permits a stylet (not shown in this view) to be disposed completely through the lead, including through electrode section 103. Also seen in cut-away in this view is needle 105.

In the preferred embodiment, needle 105 is a 20 gauge thin wall metal needle selected either from Medtronic Models 041828 or 041829 Foramen needles. Needle is also preferable insulated with a parylene coating along its outer surface but for a portion near distal end and proximal end. This permits the needle itself to electrical stimulate the nerve to assess whether the location is acceptable during the implant procedure.

Figure 5:
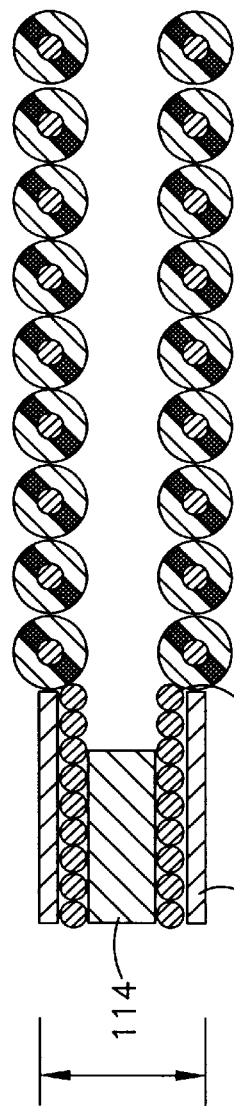
FIG. 5 is a perspective view of an additional embodiment of a medical electrical lead disposed through a needle according to the present invention.

FIG. 5 is a sectional view of the lead of FIG. 3 across a notch. As seen in this embodiment, all elements of the lead are the same as that shown in FIG. 3 but for the electrode section 113. In this embodiment, electrode section 113 is comprised of a crimp core around which the closely wound uninsulated conductor coil is crimped and which further features an outer crimp skirt.

Figure 6:
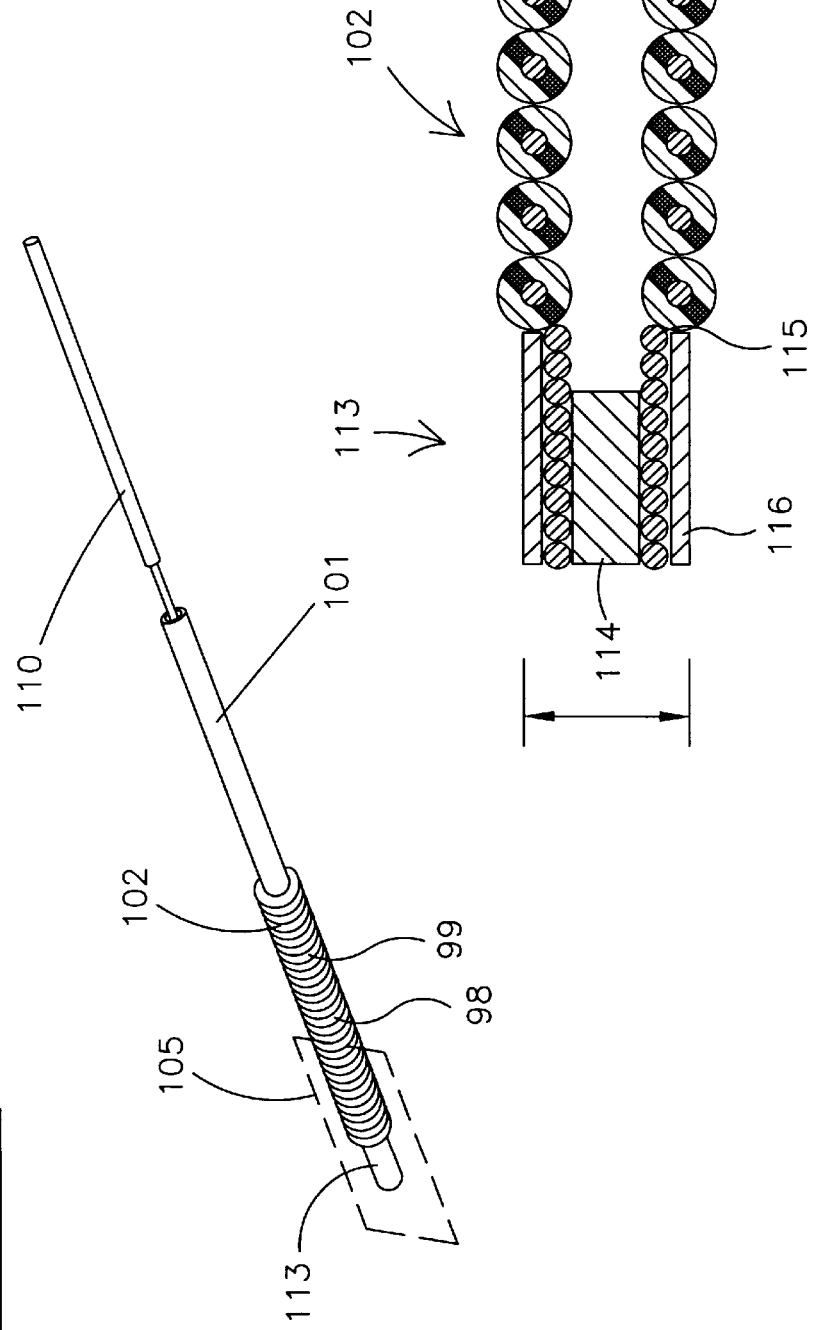
FIG. 6 is a sectional view of the distal end of the lead of FIG. 5.

FIG. 6 is a sectional view of the lead of FIG. 3 across a portion of the lead body proximal to the anchoring portion. This view shows, in detail, the crimp core, uninsulated coiled conductor and crimp skirt. In particular, crimp core 114 is comprised of a solid cylindrical stainless steel core about which the uninsulated conductor coil 115 is crimped through the use of stainless steel crimp skirt 116. In a further alternative embodiment, crimp core may be fashioned so as to include a MCRD which would elute a pharmacologic agent, such as the steroid dexamethasone. In a still further embodiment the entire lead may be treated with any desired drug which is no more than sparingly soluble in water applied to the electrode surface. This may include a steroid which is very slightly soluble in water, such as beclomethasone dipropionate anhydrous. Preferably the steroid is applied to the surface of the lead which contacts tissue when implanted. Further details of treating the lead in this manner may be found in the copending U.S. patent application of Williams entitled "Medical Electrical Lead" filed Feb. 21, 1996 having Ser. No. 08/604,591 assigned to the assignee of the present invention and incorporated herein by reference. In a still further alternative embodiment, the length of the lead may be treated with additional compounds to minimize tissue growth, including coating with gluteraldehyde. Still further the lead may be treated with anti-biotic agents, if desired, such as gentamicin.

It should be noted, in this embodiment, that the outer diameter of electrode section 113 is preferably equal to or even less than the outer diameter of lead body 102. One believed advantage of this alternative embodiment is that it prevents the stylet from being pushed through beyond the distal end of the lead body. Other possible advantages achieved by this design are both improved temporary fixation as well as a well defined effective electrode surface area.

FIG. 7 is an alternative embodiment of the lead shown in FIG. 3. As seen, all elements of this embodiment are the same as that shown in FIG. 3 but for the additional stylet handle assembly. In particular, stylet in this embodiment features a stylet handle assembly 170 which has an outer parameter cylindrical skirt 171 designed to engage and fit around and friction position lead body proximal end 102. Stylet handle assembly is preferably constructed through an outer silicon rubber cover which provides both the enhanced friction necessary for engaging with the lead body and further provides suitable friction for manipulation by the physician's hand. As seen, within outer skirt 171 is a cavity 172 diminished so as to have lead body fit therein.

FIG. 8 is a further alternative embodiment of the lead shown in FIG. 3. In this embodiment one or more sections of the lead body or electrode are not closely wound, i.e. the coils do not necessarily touch or rub against each other.

Figure 9:
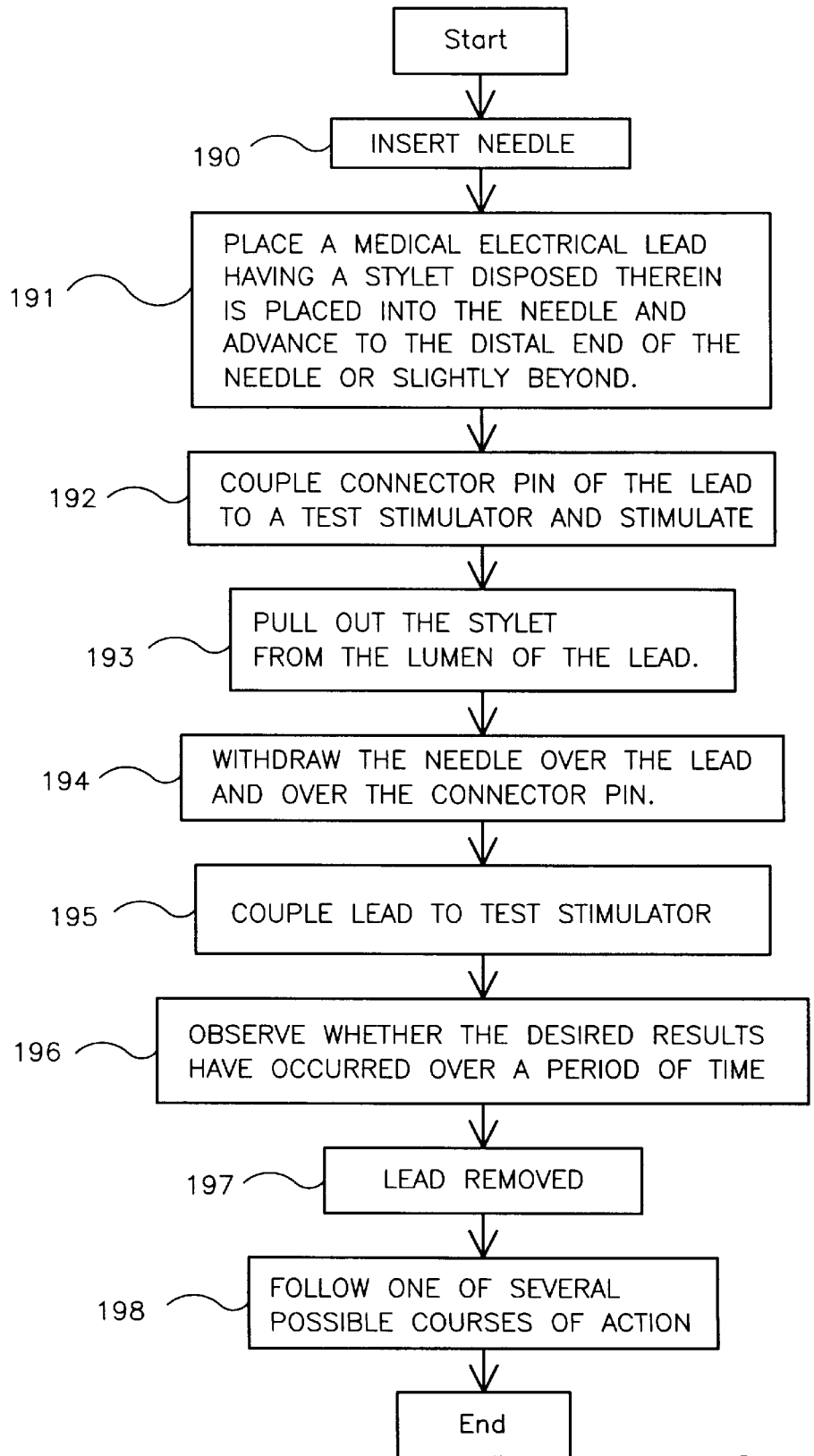
FIG. 9 depicts the steps used to implant a lead according to the present invention.

FIG. 9 depicts a further alternative embodiment of the lead shown in FIG. 3. As discussed above, the present invention is used to temporarily permit the sacral nerves to be electrically stimulated so that the ability of the patient to receive chronic sacral nerve stimulation may be assessed.

As seen at step 190, a needle is inserted into the patient and preferably into the desired area of the sacrum through a foramina. As discussed above, the needle is at least partially insulated such that its distal end or a portion of its distal end is electrically conductive. During this step the sacral nerve may be attempted to be stimulated using this portion of the needle through the coupling of the needle to an acceptable test stimulator. In the preferred embodiment, an acceptable test stimulator is the Medtronic Model 3625 test stimulator.

Next, at step 191 a medical electrical lead, according to the present invention, having a stylet disposed therein is placed into the needle and advanced to the distal end of the needle or slightly beyond. If the lead and stylet assembly is advanced beyond the needle (it is ultimately within the preference of the physician), such advancement typically would be between 1–4 mm.

Next, at step 192 a connector pin of the lead is coupled to an acceptable test stimulator and stimulation is provided. At this point the physician would know whether there are any unacceptable side effects from the stimulation or whether any initial indications of acceptable lead placement are seen. If the physician is not, at this point, satisfied the lead and needle, the stylet may be withdrawn and the process again begun back at step 190.

If step 192 has been performed with satisfactory results for the patient, the physician would then proceed to step 193 and pull out the stylet from the lumen of the lead.

Next, the physician would proceed to step 194 and withdraw the needle over the lead and, eventually, over the connector pin.

Next, the physician, in step 195, couples the lead to the test stimulator to thereafter permit an assessment to be made of sacral nerve stimulation for that particular patient, as is well known in the art.

Next, the physician, in step 196, observes whether the desired results (enhanced voiding or less incontinence, for example) have occurred over a period of time, preferably between 7 and 14 days.

Next, at step 197 the lead would be removed.

Finally at 198 one of several possible courses of action would be followed, including implanting a permanent system, or repeating steps 190–197 for another temporary lead introduced and screening begun at another location, or choosing to follow no further.

Figure 10:
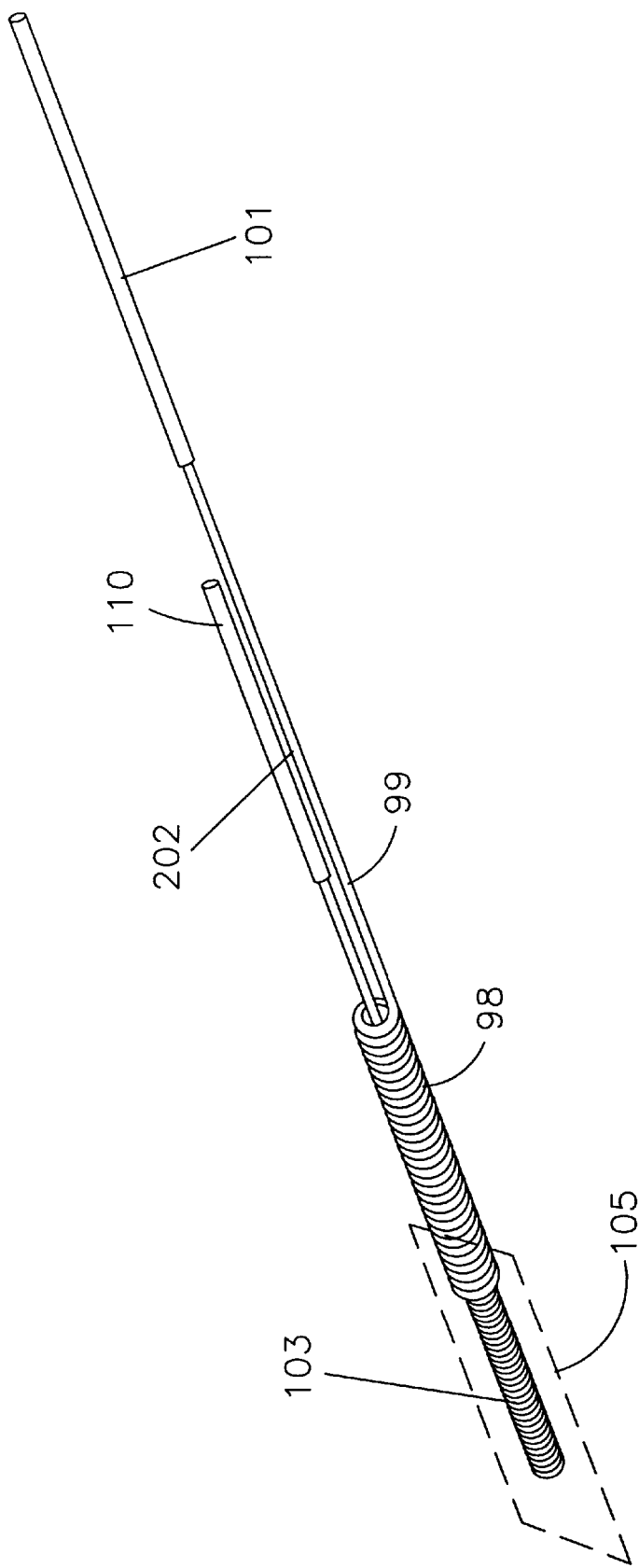
FIG. 10 is a side view of an alternative embodiment of the present invention.

FIG. 10 is a side view of an alternative embodiment of the present invention. As seen, this embodiment is the same as that shown in FIG. 3 but for the lead body 202. In particular as seen this embodiment features a lead body which is coiled in its distal end but which is straight in its proximal end. All other features of this lead, however, are the same as that shown in FIG. 3

Although the invention has been described in detail with particular reference to a preferred embodiment and alternate embodiments thereof, it will be understood variations and modifications can be effected within the scope of the following claims. Such modifications may include substituting elements or components which perform substantially the same function in substantially the same way to achieve substantially the same result for those described herein.

What is claimed is:

1. A system for providing medical electrical stimulation to at least a portion of the nervous system comprising:

a rigid hollow needle having a lumen;

a flexible lead body disposed within the lumen of the needle, the lead body having an insulated coiled proximal section and an electrode section, the proximal section comprising a coiled, insulated conductor, the conductor in the electrode section comprising coils having no outer insulation disposed thereover, the electrode section further comprising a crimp core to which a distal end of the coiled conductor is crimped, the electrode section having a surface area of about 11 sq. mm.

2. The system according to claim 1, wherein the electrode section has a length of 10 mm.

3. The system according to claim 2, wherein the electrode section wherein the coiled conductor is closely wound.

4. The system according to claim 3, wherein the electrode section is closely wound.

5. The system according to claim 1, wherein the electrode section wherein the rigid hollow needle is partially covered along its outer surface with an insulation.

6. The system according to claim 5, wherein the insulation is parylene.

7. The system according to claim 1, wherein the rigid hollow needle has a proximal section and a distal section, electrical insulation being disposed in an area between the proximal section and the distal section.

8. The system according to claim 1, wherein the flexible lead body has a lumen therein, a stylet disposed within the lead body.

9. The system according to claim 1, wherein the stylet has a stylet body dimension to fit within the lumen, and a stylet handle, the handle dimension to fit over an exterior surface of the lead body distal end and engage thereto.

10. The system according to claim 1, further comprising means for electrically coupling the electrical conductor to a pulse generator, the means for electrical coupling located on a proximal end of the lead body wherein the means comprise a connector pin, the connector pin sized to fit within the lumen.

11. The system according to claim 1, further comprising means for anchoring the electrode within the sacrum, the anchoring means integral with the electrode section.

12. The system according to claim 1, further comprising means for providing longitudinal strain relief from strain exerted near the proximal end of the lead body from being transmitted to the electrode section of the lead body.

13. A system for providing medical electrical stimulation to at least a portion of the nervous system comprising:

a rigid hollow needle having a lumen;

a flexible lead body disposed within the lumen of the needle, the lead body having an insulated coiled proximal section and an electrode section, the proximal section comprising a coiled, insulated conductor, the conductor in the electrode section comprising coils having no outer insulation disposed thereover, the electrode section further comprising a crimp core to which a distal end of the coiled conductor is crimped, the electrode section having a surface area of about 11 sq. mm.

14. The system according to claim 13, wherein the electrode section has a length of 10 mm.

15. The system according to claim 13, wherein the coiled conductor is closely wound.

16. The system according to claim 13, wherein the electrode section wherein the rigid hollow needle is partially covered along its outer surface with all insulation.

17. The system according to claim 16, wherein the insulation is parylene.

18. The system according to claim 16, wherein the rigid hollow needle has a proximal section and a distal section, electrical insulation being disposed in an area between the proximal section and the distal section.

19. The system according to claim 13, wherein the flexible lead body has a lumen therein, a stylet disposed within the lead body.

20. The system according to claim 19, wherein the stylet has a stylet body dimension to fit within the lumen, and a stylet handle, the handle dimension to fit over an exterior surface of the lead body distal end and engage thereto.

21. The system according to claim 13, further comprising means for anchoring the electrode within the sacrum, the anchoring means integral with the electrode section.

22. The system according to claim 13, further comprising means for providing longitudinal strain relief from strain exerted near the proximal end of the lead body from being transmitted to the electrode section of the lead body.

* * * * *